(12) United States Patent
Barr et al.

(10) Patent No.: US 7,323,290 B2
(45) Date of Patent: *Jan. 29, 2008

(54) DRY FILM PHOTORESIST

(75) Inventors: Robert K. Barr, Shrewsbury, MA (US); Edgardo Anzures, Westborough, MA (US); Daniel E. Lundy, Winchendon, MA (US)

(73) Assignee: Eternal Technology Corporation, Colonia Heights, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/391,051

(22) Filed: Mar. 18, 2003

(65) Prior Publication Data

US 2004/0063026 A1    Apr. 1, 2004

Related U.S. Application Data

(60) Provisional application No. 60/432,875, filed on Dec. 12, 2002, provisional application No. 60/414,758, filed on Sep. 30, 2002, provisional application No. 60/414,759, filed on Sep. 30, 2002.

(51) Int. Cl.
*G03F 7/038* (2006.01)
*G03F 7/028* (2006.01)
*G03F 7/033* (2006.01)

(52) U.S. Cl. .............. 430/285.1; 430/286.1; 430/287.1; 430/916; 522/34; 522/35; 522/905; 522/904

(58) Field of Classification Search ............. 430/270.1, 430/926, 913, 285.1, 286.1, 287.1, 916; 522/34, 522/35, 904, 905
See application file for complete search history.

(56) References Cited

U.S. PATENT DOCUMENTS

| | | | |
|---|---|---|---|
| 3,620,733 A * | 11/1971 | Hartmut et al. .......... 430/285.1 |
| 4,040,925 A | 8/1977 | McGinniss |
| 4,186,069 A | 1/1980 | Muzyczko et al. |
| 4,224,398 A | 9/1980 | Muzyczko et al. |
| 4,273,851 A | 6/1981 | Muzyczko et al. |
| 4,537,855 A | 8/1985 | Ide |
| 4,795,787 A | 1/1989 | Walz |
| 4,910,119 A | 3/1990 | Schneller et al. |
| 4,912,018 A | 3/1990 | Osuch et al. |
| 4,992,354 A | 2/1991 | Axon et al. |
| 5,037,913 A | 8/1991 | Leussler et al. |
| 5,068,262 A | 11/1991 | Noguchi |
| 5,070,118 A * | 12/1991 | Eckberg ....................... 522/99 |
| 5,108,870 A | 4/1992 | Shalom |
| 5,153,323 A | 10/1992 | Rossman et al. |
| 5,376,503 A * | 12/1994 | Audett et al. ............ 430/270.1 |
| 5,415,972 A | 5/1995 | Mayes |
| 5,492,790 A | 2/1996 | Hishiro |
| 5,683,856 A | 11/1997 | Aoai et al. |
| 5,712,078 A | 1/1998 | Huang et al. |
| 5,719,008 A | 2/1998 | Hozumi et al. |
| 5,723,513 A * | 3/1998 | Bonham et al. .............. 522/63 |
| 5,733,714 A | 3/1998 | McCulloch et al. |
| 5,741,829 A * | 4/1998 | Reich et al. .................. 522/35 |
| 5,869,220 A | 2/1999 | Hallock et al. |
| 5,945,489 A | 8/1999 | Moy et al. |
| 6,011,077 A * | 1/2000 | Muller ......................... 522/35 |
| 6,025,410 A | 2/2000 | Moy et al. |
| 6,151,042 A * | 11/2000 | Smith et al. .................. 347/20 |
| 6,153,349 A | 11/2000 | Ichikawa et al. |
| 6,156,345 A * | 12/2000 | Chudzik et al. ............ 424/484 |
| 6,165,677 A | 12/2000 | Yako |
| 6,207,356 B1 | 3/2001 | Banba et al. |
| 6,242,597 B1 | 6/2001 | Gupta et al. |
| 6,251,569 B1 | 6/2001 | Angelopoulos et al. |
| 6,294,591 B1 * | 9/2001 | Blum et al. .................. 522/35 |
| 6,297,328 B1 | 10/2001 | Collins et al. |
| 6,406,828 B1 | 6/2002 | Szmanda et al. |
| 6,455,479 B1 | 9/2002 | Sahbari |
| 6,458,517 B2 | 10/2002 | Nohara et al. |
| 2004/0013895 A1 * | 1/2004 | Dean et al. .................. 428/515 |
| 2004/0063027 A1 * | 4/2004 | Barr et al. ............... 430/270.1 |

FOREIGN PATENT DOCUMENTS

| | | |
|---|---|---|
| EP | 0 469 584 B1 | 3/1997 |
| EP | 1 008 911 | 6/2000 |
| EP | 1 336 630 | 8/2003 |
| EP | 1 403 708 | 3/2004 |
| EP | 1 403 709 | 3/2004 |

\* cited by examiner

*Primary Examiner*—Richard L. Schilling
(74) *Attorney, Agent, or Firm*—Scully, Scott, Murphy & Presser, P.C.

(57) ABSTRACT

A dry film photoresist includes a functional polymer. The functional polymer has α,β-unsaturated groups and groups that generate a free radical upon exposure to actinic radiation.

6 Claims, No Drawings

DRY FILM PHOTORESIST

This application claims the benefit of U.S. Provisional Application(s) No(s).: Application No(s).: 60/4 14 759 filing date Sep. 30, 2002 Application No. 60/414,758 filing date Sep. 30, 2002 Application No. 60/432,875 filing date Dec. 12, 2002

BACKGROUND OF THE INVENTION

The present invention is directed to a dry film photoresist. More specifically, the present invention is directed to a dry film photoresist containing a polymer having unsaturated groups and that generates a free radical.

A dry film photoresist may be either positive working or negative working. Negative working photoresists exposed to activating radiation polymerize or cross-link in a reaction between a photoactive compound and polymerizable agents of the photoresist composition. Consequently, the exposed coating portions are rendered less soluble in a developer solution than unexposed portions. For positive working photoresists, exposed portions are rendered more soluble in a developer solution while areas not exposed remain comparatively less developer soluble.

Dry film photoresists also may be primary photoimaging resists or secondary photoimaging resists. Primary photoresists are used to form temporary coatings on substrates. Secondary photoresists are hardenable and form permanent layers, e.g., solder masks. Photoresists are used to make printed circuits, printing plates, solder masks and the like. Photoresists have various requisites such as etching resistance, heat resistance, adhesion and developable in developer solutions such as alkaline solutions.

Dry film photoresists include at least a resin binder, a cross-linking monomer or oligomer and a photoinitiator. A wide variety of polymeric binders may be employed in dry film photoresists. Such polymeric binders may include, as polymerized components, one or more acid functional monomers such as acrylic acid or methacrylic acid. Polymeric binders take up space in the photoresist and are passively linked to the cross-linking monomers or oligomers. Photoinitiators initiate the cross-linking reaction between the cross-linking monomers or oligomers upon exposure to light. Other additives included in photoresists are anti-striation reagents, plasticizers, speed enhancers, surfactants, fillers, and dyes.

Dry film photoresists may be laminated to a substrate. Such dry film photoresists are particularly suitable for use in printed wiring board manufacture. One problem with many dry film photoresists is that they are difficult to strip from electrolytically plated circuit boards using conventional alkaline aqueous stripping solutions, e.g. 3% sodium hydroxide solutions. If the photoresist is not completely stripped and removed, ragged metal circuit lines may result after etching which may cause short-circuiting of the board.

Many manufacturers use organic-based (amine- or organic solvent-containing) alkaline stripping solutions that produce a smaller stripped particle to facilitate stripping. While the organic strippers, e.g., solutions containing trimethylamine or tetramethylammonium hydroxide, remove the photoresist, such strippers are expensive relative to alkaline aqueous strippers (sodium hydroxide and potassium hydroxide), and have more waste treatment and environmental concerns associated with them. Further, due to emphasis in the industry on reducing solvent emissions in the workplace, solvent-strippable photoresists are much less desirable than the aqueous-strippable.

Instability of a dry film photoresist composition results in a short shelf life. Instability may result from the cross-linking monomers included in the photoresist composition. Prior to exposure of a photoresist composition to actinic radiation, each monomer is a potential reactant with another monomer. If not properly stored or when the photoresist is prematurely exposed to a radiation source, the monomers may prematurely react, thus spoiling the composition and reducing shelf life. Also, after exposure of the photoresist composition to actinic radiation, a fair proportion of the cross-linking monomers may not react. Thus, improper curing of the photoresist may occur resulting in brittle or poorly chemically resistant photoresist.

Additionally, cross-linking monomers or oligomers may precipitate out of the dry film during storage. This phenomena is known as cold flow. Dry film is often stored in rolls. When the cross-linking agents precipitate out and then dry along the sides of the roll, a seal of dry monomers is formed that prevents the dry film from being unrolled prior to use.

Another problem associated with many dry film photoreisists is the build-up of organic sucm and residue from uncured photoresist. Such organic scum and residue may deposit on various articles and apparatus during the manufacture of products made using photoresists such as printed wiring boards, developer solutions and developer apparatus. Much of the organic scum and residue is caused by unsaturated monomers and oligomers such as (meth)acrylate-based compounds and photoactive agents having numerous aromatic groups. Examples of such photoactive agents that may form part of the scum and residue include, but are not limited to, imidazole dimmers, benzophenones, acetophenones, anthraquinones, naphthaquinones, and triazine-based compounds. Such contaminants are not readily water-soluble or water-dispersable after they form residues in solution or deposit on an article or apparatus. As dissolved photoresists build up in solution (developer loading) insoluble organic materials begin to form in the developing tank eventually forming scum or residue. Presence of anti-foam additives (added to developer solutions to minimize foaming) greatly increases the tendency for residue and scum to form. As the level of scum builds chances increase for a redeposit of the scum and residue onto the developed circuit board. Such redeposited residues cause a retardation of etching solution (etching chemistries have difficulty penetrating organic residues). Where etch is retarded, circuit shorts form causing a defective circuit board. In addition to increasing potential for defective circuit boards, the residue and scum also make cleaning equipment difficult, thus increasing maintenance time and cost.

U.S. Pat. No. 5,945,489 and U.S. Pat. No. 6,025,410 both to Moy et al. (also see "Novel Resins That Cure Without Added Photoinitiator" by Sheridan et al. Chemistry III-New Chemistry, RadTech 2002, pages 462-474 (Technical Conference Proceedings)) disclose photosensitive oligomers that may be cross-linked without added photoinitiator. The patents disclose that a Michael addition of acetoacetate donors to multifunctional acrylate receptor compounds yields polyesters with reactive pendent acrylate groups, which may be cross-linked in a subsequent curing reaction. The patents state that pendent methyl ketone substituents serve as an internal photoinitiator. Upon exposure to UV radiation, an acyl radical with the methyl substituent is believed to be formed which acts as a photoinitiator, thus photoinitiators are not added to compositions containing the oligomers. Such oligomers are liquid oligomers, which may be employed as decorative coatings on wood and metal substrates. Odor generated from unreacted photoinitiators and skin absorption of unreacted photoinitiators is avoided, thus compositions containing such oliogmers may be employed in materials that include medical and food contact applications. However, such oligomers are not believed to be suitable for use in photoresists because they are not alkali developable, and are not photosensitive at wavelengths greater than 320 nm. Accordingly, the oligomers of Moy et al. are limited in their applications.

Accordingly, there is a need for a dry film photoresist that eliminates or at least reduces the foregoing problems.

SUMMARY OF THE INVENTION

The present invention is directed to dry film photoresists having polymers with $\alpha,\beta$-unsaturation and functional groups that generate free radicals upon exposure of the photoresists to actinic radiation, the polymers have average molecular weights of at least 1000 daltons.

The $\alpha,\beta$-unsaturated functional groups of the polymers enable the polymers to self-cross-link, thus compositions containing the polymers have no additional unsaturated monomers or at least have reduced amounts of unsaturated monomers in contrast to many conventional photoreactive compositions. Also the free radicals generated by the polymers may act as photoinitiators, thus dry films of the present invention eliminate or reduce the amounts of added photoinitiator in contrast to conventional dry film photoresists.

The polymers may have hydrophilic components such that the polymers are water-soluble or water-dispersable. When such polymers are included in dry film photoresists of the present invention, they improve the water-solubility or water-dispersability of the dry film. Such improved water-solubility or water-dispersability eliminates or at least reduces scum and residue formation. Further, the hydrophilicity of the dry film also improves its developability and strippability.

In addition to $\alpha,\beta$-unsaturation and an integral photoinitiator, the polymers may have dyes, stripping agents, plasticizers, surfactants and other components used in photoresists joined to them.

DETAILED DESCRIPTION OF THE INVENTION

A "moiety" within the scope of the present invention means a distinct structural component of the functionlized polymer and is synonymous with the term "group". The term "polymer" means both polymer and copolymer. A "capping group" is a group that is at a terminus of a polymer's backbone. "Pendent" means a structural component of the functionalized polymer that is joined to or suspended from the main chain or backbone of the functionalized polymer by a chemical bond. "(Meth)acrylate" means both acrylate and methacrylate and (meth)acrylic means both acrylic and methacrylic. "Monomer" or "oligomer" means any ethylenically or acetylenically unsaturated compound that may be polymerized. "Functional group" means a component of a functional polymer that adds serviceability or processability to the polymer or permits the polymer to have a function in a composition other than just as a binder component. "Hydrophilic" within the scope of the present invention means water-soluble or water-dispersable. "Water-soluble" within the scope of the present invention means that a compound or polymer swells or dissolves in water at normal temperatures (from above 0° C. to 100° C. at 1 atomosphere pressure). "Water-dispersable" within the scope of the present invention means that a compound or polymer forms an emulsion, micro-emulsion or suspension in water at normal temperatures. All numerical ranges are inclusive and combinable in any order, except where it is logical that such numerical ranges are constrained to add up to 100%.

Dry film photoresists of the present invention include polymers that have $\alpha,\beta$ unsaturation, functional groups that generate free radicals upon exposure of the photoresist to actinic radiation and have average molecular weights of at least 1000 daltons. The polymers having the $\alpha,\beta$-unsaturation and functional groups that generate a free radical are film forming functional polymers. The film forming functional polymers have a main chain or backbone that is derived from $\alpha,\beta$-ethylenically or acetylenically unsaturated polymerizable monomers or oligomers or combinations thereof and terminate with at least one free unsaturated group at either end of the polymer.

In addition to the at least one free unsaturated group at either end of the polymer, at least one monomer or oligomer employed to make the polymer backbone may have one or more groups that are free to react with another compound to join that other compound to the polymer backbone to form a pendent functional group. Pendent functional groups may terminate in one or more $\alpha,\beta$-ethylenically or acetylenically unsaturated functional group or another type of functional group. Functional groups enable the polymer to self cross-link, generate a free radical, make the polymer hydrophilic or to add additional functional components to the polymer. Functional groups make the polymer and compositions in which the polymer is used serviceable or processable. Serviceable, for example, means that the polymer and compositions in which the polymer is used may be coated on a substrate, durable against solutions such as plating solutions, has less post-exposure back cross-linking, or is sensitive to light at wavelengths of at least 300 nm. Processability, for example, means that the polymer and compositions in which the polymer is used may be developed, stripped, or have an affinity for adhesion to metals. Compounds that may be joined to the polymer to form functional groups or moieties on the polymer include, but are not limited to, photoinitiators, plasticizers, surfactants, dyes, stripping agents or combinations thereof. Any compound or component that may be joined to a polymer to improve the serviceability or processability of the polymer or a composition in which the polymer is used may be employed to practice the present invention. Examples of such compounds are disclosed below.

Functional polymers may be prepared by any suitable method know in the art. One method of preparing functional polymers is to first functionalize one or more monomers or oligomers that are employed to compose the polymer backbone followed by free radical polymerization of the monomers or oligomers or combinations thereof, thus forming a polymer with pendent functional groups. For example, monomers or oligomers having hydroxyl (—OH), carboxyl (—COOH), or ester (—COOR, where R is an organic moiety) groups may react with compounds having free hydroxyl groups, carboxyl groups, ester groups, aminyl (—$NH_2$ or NHR), or isocyanate (—NCO) groups to form pendent groups. Examples of such reactions include addition reactions or condensation reactions. Examples of such addition reactions include nucleeophilic, electrophilic and free-radical addition reaction. Other examples of reactions include, but are not limited to, ether formation, transesterification, anhydride formation, amide formation or urea formation. Such reaction methods and conditions to carry out reactions are well known in the art. See Morrison and Boyd, "Organic Chemistry", $3^{rd}$ edition, New York University, 1973; and March, "Advanced Organic Chemistry, Reactions, Mechanisms, and Structure." $2^{nd}$ edition, McGraw Hill Company, 1977. Free radical polymerization of the monomers or oligomers or combinations thereof follows to form a functional polymer. Conditions for free radical polymerization of monomers and oligomers are well known in the art. For example, free radical polymerization of functional monomers or oligomers may be performed in suspension solution (from 60° C. to 80° C.) or emulsion (from −20° C. to 60° C.) form. Pressures employed are near or at 1 atmosphere. Peroxide initiators may be employed in the polymerization process such as dibenzoyl peroxide. Azo initiators also may be employed such as 2,2'-azobis(2-methylpropanenitrile) or 2,2' azobis(2-methylbutane-nitrile).

Alternative processes for preparing a functional polymer are anionic polymerization, condensation polymerization, or by post polymerization functionalization. In post polymerization functionalization, the main chain or backbone and the functional pendent components are prepared separately. Monomers or oligomers or combinations thereof, which compose the backbone, may be joined by free radical polymerization. Compounds that compose the functional pendent groups may be prepared by any suitable method known in the art. Such compounds need only have one free reactive group as described above to bond with a free reactive group on the polymer backbone. After the synthesis of the separate components that make up the polymer, they are then joined together in a separate reaction process to form the final functional polymer product. Examples of chemical bonds formed between a polymer backbone and a pendent functional group are an ether bond R—O—P, where R is as defined above and P is a polymer backbone, an ester bond P—COO—R, or RCOO—P.

Another example of such a reaction is between an isocyanate compound and a reactive group from a polymer backbone. After the polymer backbone is prepared, the polymer backbone is mixed with an isocyanate compound at reaction temperatures below 80° C. Mixing and heating are continued until the reaction is complete. Typically, the reaction continues for 1 hour to 8 hours. Reactions that take place occur between a free isocyanate group on the isocyanate compound and a hydroxyl group, carboxyl group, or primary or secondary aminyl functional group attached to the polymer backbone. One mole of free isocyanate reacts with one mole of a hydroxyl, carboxyl, or primary or secondary aminyl on the polymer main chain. The reaction may be self quenching. Water, alcohol, or other chemical speicies with labile hydrogen, and a suitable catalyst, such as triethylamine, may be added at the end of the reaction to quench any free isocyanate. Also, a suitable polymerization inhibitor may optionally be added to prevent premature cross-linking of terminal ethylenically or acetylenically unsaturated moieties such as a (meth)acrylate moiety. Reaction completion may be determined by using standard analytical instruments well known in the art.

The synthesis may be carried out in the presence of an inert dry solvent (inert to reaction conditions), for example, an ether, an ester, ketones, nitriles, sulfones, and phosphoric acid esters. To accelerate the reactions of the methods of the present invention, any suitable catalyst employed in polymerization reactions can be used. Tin containing catalysts are an example. Stabilizers or polymerization inhibitors may optionally be added to the reaction steps to stabilize free-radical polymerization.

Free isocyanate, i.e., —N═C═O, reacts with a hydroxyl group from the polymer backbone, or a hydroxyl group from a carboxyl group from the polymer backbone to form a R—NH—C(O)—P linkage where P is the polymer backbone, and R is an organic moiety. Examples of R include, but are not limited to, substituted and unsubstituted alkyl, aryl, alkylaryl or cycloaliphatic. Other specific examples include a urethane group containing compound such as a biuret group. A free isocyanate that reacts with a primary or secondary amine moiety joined to the polymer backbone forms a R—NH—C(O)—NR$^1$-G-P urea (carbamide) linkage where R$^1$ includes, but is not limited to, hydrogen, a linear, branched or unsubstituted or substituted alkyl, or an unsubstituted or substituted aryl. Substituent groups include, but are not limited to, halogen, such as fluorine, bromine, chloride or iodine, hydroxyl, carboxyl, or primary or secondary amine. A substituent group replaces a hydrogen on a carbon atom. G is an organic moiety that joins the nitrogen to the polymer chain. G includes, but is not limited to, an alkyl, or a substituted aryl where the nitrogen is joined to the aryl by an alkyl chain. The alkyl of G may be linear or branched ($C_{1-C24}$) alkyl. A free isocyanate that reacts with a polyalkoxylated moiety from the polymer backbone forms a R—NH—C(O)—O(AO)$_x$—C(O)—P linkage where A is a linear or branched ($C_1$-$C_{24}$)alkyl, and x is an integer from 0 to 1,000, preferably from 1 to 200. R, as defined above, may terminate in one or more functional groups such as ethylenically or acetylenically unsaturated moieties that permit functionalized polymers of the present invention to self cross-link.

The main chain or backbone of functionalized polymers of the present invention may be derived from monomers or oligomers which include, but are not limited to, acid functional monomers, base functional monomers, water-soluble functional monomers, urethane oligomers or mixtures thereof.

Examples of suitable ethylenically or acetylenically unsaturated monomers include, but are not limited to: (meth)acrylic acid, (meth)acrylamides, alkyl (meth)acrylates, alkenyl (meth)acrylates, aromatic (meth)acrylates, vinyl aromatic monomers, nitrogen-containing compounds and their thio-analogs, substituted ethylene monomers, cyclic olefins, substituted cyclic olefins, and the like. Preferred monomers include (meth)acrylic acid, alkyl (meth)acrylates and vinyl aromatic monomers.

Typically, the alkyl (meth)acrylates useful in the present invention are ($C_1$-$C_{24}$)alkyl (meth)acrylates. Suitable alkyl (meth)acrylates include, but are not limited to, "low cut" alkyl (meth)acrylates, "mid cut" alkyl (meth)acrylates and "high cut" alkyl (meth)acrylates.

"Low cut" alkyl (meth)acrylates are typically those where the alkyl group contains from 1 to 6 carbon atoms. Suitable low cut alkyl (meth)acrylates include, but are not limited to: methyl methacrylate, methyl acrylate, ethyl acrylate, propyl methacrylate, butyl methacrylate, butyl acrylate, isobutyl methacrylate, hexyl methacrylate, cyclohexyl methacrylate, cyclohexyl acrylate and mixtures thereof.

"Mid cut" alkyl (meth)acrylates are typically those where the alkyl group contains from 7 to 15 carbon atoms. Suitable mid cut alkyl (meth)acrylates include, but are not limited to: 2-ethylhexyl acrylate ("EHA"), 2-ethylhexyl methacrylate, octyl methacrylate, decyl methacrylate, isodecyl methacrylate (based on branched ($C_{10}$)alkyl isomer mixture), undecyl methacrylate, dodecyl methacrylate (also known as lauryl methacrylate), tridecyl methacrylate, tetradecyl methacrylate (also known as myristyl methacrylate), pentadecyl methacrylate and mixtures thereof. Particularly useful mixtures include dodecyl-pentadecyl methacrylate, a mixture of linear and branched isomers of dodecyl, tridecyl, tetradecyl and pentadecyl methacrylates; and lauryl-myristyl methacrylate.

"High cut" alkyl (meth)acrylates are typically those where the alkyl group contains from 16 to 24 carbon atoms. Suitable high cut alkyl (meth)acrylates include, but are not limited to: hexadecyl methacrylate, heptadecyl methacrylate, octadecyl methacrylate, nonadecyl methacrylate, cosyl methacrylate, eicosyl methacrylate and mixtures thereof. Particularly useful mixtures of high cut alkyl (meth)acrylates include, but are not limited to: cetyl-eicosyl methacrylate, which is a mixture of hexadecyl, octadecyl, cosyl and eicosyl methacrylate; and cetyl-stearyl methacrylate, which is a mixture of hexadecyl and octadecyl methacrylate.

The mid-cut and high-cut alkyl (meth)acrylate monomers described above are generally prepared by standard esterification procedures using technical grades of long chain aliphatic alcohols, and these commercially available alcohols are mixtures of alcohols of varying chain lengths containing between 10 and 15 or 16 and 20 carbon atoms in the alkyl group. Examples of these alcohols are the various Ziegler catalyzed ALFOL alcohols from Vista Chemical company, i.e., ALFOL 1618 and ALFOL 1620, Ziegler catalyzed various NEODOL alcohols from Shell Chemical Company, i.e. NEODOL 25L, and naturally derived alcohols such as Proctor & Gamble's TA-1618 and CO-1270. Consequently, for the purposes of this invention, alkyl (meth) acrylate is intended to include not only the individual alkyl (meth)acrylate product named, but also to include mixtures of the alkyl (meth)acrylates with a predominant amount of the particular alkyl (meth)acrylate named.

The alkyl (meth)acrylate monomers useful in the present invention may be a single monomer or a mixture having different numbers of carbon atoms in the alkyl portion. Also, the (meth)acrylamide and alkyl (meth)acrylate monomers useful in the present invention may optionally be substituted. Suitable optionally substituted (meth)acrylamide and alkyl (meth)acrylate monomers include, but are not limited to: hydroxy $(C_2-C_{20})$alkyl (meth)acrylates, dialkylamino $(C_2-C_{20})$alkyl (meth)arylates, dialkaylamino $(C_2-C_{20})$alkyl (meth)acrylamides, preferably, hydroxy$(C_2-C_6)$alkyl (meth)acrylates, dialkylamino$(C_2-C_6)$alkyl (meth)acrylates, dialkylamino$(C_2-C_6)$alkyl (meth)acrylamides.

Particularly useful substituted alkyl (meth)acrylate monomers are those with one or more hydroxyl groups in the alkyl radical, especially those where the hydroxyl group is found at the β-position (2-position) in the alkyl radical. Hydroxyalkyl (meth)acrylate monomers in which the substituted alkyl group is a $(C_2-C_6)$alkyl, branched or unbranched, are preferred. Suitable hydroxyalkyl (meth)acrylate monomers include, but are not limited to: 2-hydroxyethyl methacrylate ("HEMA"), 2-hydroxyethyl acrylate ("HEA"), 2-hydroxypropyl methacrylate, 1-methyl-2-hydroxyethyl methacrylate, 2-hydroxy-propyl acrylate, 1-methyl-2-hydroxyethyl acrylate, 2-hydroxybutyl methacrylate, 2-hydroxybutyl acrylate and mixtures thereof.

Hydroxy poly opened-ring lactone polyalkylene oxide (meth)acrylates as described in U.S. Pat. No. 6,045,973 may be employed. Suitable hydroxy polyalkylene oxide (meth) acrylates may be prepared from poly(propylene glycol) (meth)acrylates, poly(propylene glycol) alkyl ether (meth) acrylates, poly (propylene glycol) phenyl ether (meth)acrylates, poly(propylene glycol) 4-nonylphenol ether (meth) acrylates, poy(ethylene glycol) (meth)acrylates, poly (propylene/ethylene glycol) (meth)acrylates, poly(ethylene glycol)alkyl ether (meth)acrylates, poly(ethylene glycol) phenyl ether (meth)acrylates, poly(propylene/ethylene glycol) alkylether (meth)acrylates and mixtures thereof may be employed. The poly(alkylene oxide) may have from 1 to 50 degrees of polymerization. Such compounds may also be joined to the polymer backbone as a pendent functional group via an isocyanate group by reacting the hydroxyl of the poly (alkylene oxide) with an isocyanate of a polyisocyanate. A free isocyanate may then be reacted with a reactive group on the polymer to join it to the polymer.

Other substituted monomers useful in the present invention are those with a tertiary amino group or alkylamino group. Examples include, but are not limited to: dimethylaminoethyl methacrylate, dimethylaminoethyl acrylate, N-methylaminoethyl methacrylamide, N-methyl-aminopropyl methacrylamide, N-methylaminobutyl methacrylamide, N-ethylaminoethyl methacrylamide, N-ethylaminopropyl methacrylamide, N-ethylaminobutyl methacrylamide, N-(1, 1-dimethyl-3-oxobutyl) acrylamide, N-(1,3-diphenyl-1-ethyl-3-oxobutyl) acrylamide, N-(1-methyl-1-phenyl-3-oxobutyl) methacrylamide, and 2-hydroxyethyl acrylamide, N-methacrylamide of aminoethyl ethylene urea, N-maleimide of dimethylaminopropylamine and mixtures thereof.

Other substituted (meth)acrylate monomers useful in the present invention are silicon-containing monomers such as y-propyl tri$(C_1-C_6)$alkoxysilyl (meth)acrylate, y-propyl tri$(C_1-C_6)$alkylsilyl (meth)acrylate, γ-propyl di$(C_1-C_6)$alkoxy$(C_1-C_6)$alkylsilyl (meth)acrylate, y-propyl di$(C_1-C_6)$alkyl$(C_1-C_6)$alkoxysilyl (meth)acrylate, vinyl tri$(C_1-C_6)$alkoxysilyl (meth)acrylate, vinyl di$(C_1-C_6)$alkoxy$(C_1-C_6)$alkylsilyl (meth)acrylate, vinyl $(C_1-C_6)$alkoxydi$(C_1-C_6)$alkylsilyl (meth)acrylate, vinyl tri$(C_1-C_6)$alkylsilyl (meth) acrylate, 2-propylsilsesquioxane (meth)acrylate and mixtures thereof.

The vinyl aromatic monomers useful as unsaturated monomers in the present invention include, but are not limited to: styrene, hydroxystyrene, a-methylstyrene, vinyltoluene, p-methylstyrene, ethylvinylbenzene, vinylnaphthalene, vinylxylenes, and mixtures thereof. The vinylaromatic monomers also include their corresponding substituted counterparts, such as halogenated derivatives, i.e., containing one or more halogen groups, such as fluorine, chlorine or bromine; and nitro, cyano, $(C_1-C_{10})$alkoxy, halo$(C_1-C_{10})$ alkyl, carb$(C_1-C_{10})$alkoxy, carboxy, amino, $(C_1-C_{10})$alkylamino derivatives and the like.

The nitrogen-containing compounds and their thio-analogs useful as unsaturated monomers in the present invention include, but are not limited to: vinylpyridines such as 2-vinylpyridine or 4-vinylpyridine; $(C_1-C_8)$alkyl substituted N-vinyl pyridines such as 2-methyl-5-vinyl-pyridine, 2-ethyl-5-vinylpyridine, 3-methyl-5-vinylpyridine, 2,3-dimethyl-5-vinyl-pyridine, and 2-methyl-3-ethyl-5-vinylpyridine; methyl-substituted quinolines and isoquinolines; N-vinylcaprolactam; N-vinylbutyrolactam; N-vinylpyrrolidone; vinyl imidazole; N-vinyl carbazole; N-vinyl-succinimide; (meth)acrylonitrile; o-, m-, orp-aminostyrene; hydroxystylene; maleimide; N-vinyl-oxazolidone; N,N-dimethyl aminoethyl-vinyl-ether; ethyl-2-cyano acrylate; vinyl acetonitrile; N-vinylphthalimide; N-vinyl-pyrrolidones such as N-vinyl-thio-pyrrolidone, 3 methyl-1-vinyl-pyrrolidone, 4-methyl-1-vinyl-pyrrolidone, 5-methyl-1-vinyl-pyrrolidone, 3-ethyl-1-vinyl-pyrrolidone, 3-butyl-1-vinyl-pyrrolidone, 3,3-dimethyl-1-vinyl-pyrrolidone, 4,5-dimethyl-1-vinyl-pyrrolidone, 5,5-dimethyl-1-vinyl-pyrrolidone, 3,3,5-trimethyl-1-vinyl-pyrrolidone, 4-ethyl-1-vinyl-pyrrolidone, 5-methyl-5-ethyl-1-vinyl-pyrrolidone and 3,4,5-trimethyl-1-vinyl-pyrrolidone; vinyl pyrroles; vinyl anilines; and vinyl piperidines.

The substituted ethylene monomers useful as unsaturated monomers in the present invention include, but are not limited to: vinyl formamide, vinyl chloride, vinyl fluoride, vinyl bromide, tetrafluoroethylene, trifluoroethylene, vinyl ethers and itoconic anhydride.

Suitable cyclic olefin monomers useful in the present invention are ($C_5$-$C_{10}$) cyclic olefins, such as cyclopentene, cyclopentadiene, dicylopentene, cyclohexene, cyclohexadiene, cycloheptene, cycloheptadiene, cyclooctene, cyclooctadiene, norbornene, maleic anhydride and the like. Such cyclic olefins also include spirocyclic olefin monomers such as spirocyclic norbornenyl monomers, spirocyclic cyclohexene monomers, spirocyclic cyclopentene monomers and mixtures thereof. Suitable substituted cyclic olefin monomers include, but are not limited to, cyclic olefins having one or more substituent groups selected from hydroxy, aryloxy, halo, ($C_1$-$C_{12}$)alkyl, ($C_1$-$C_{12}$)haloalkyl, ($C_1$-$C_{12}$)hydroxyalkyl, ($C_1$-$C_{12}$)halohydroxyalkyl such as $(CH_2)_{n'}C(CF_3)_2OH$ where n'=0 to 4, ($C_1$-$C_{12}$)alkoxy, thio, amino, ($C_1$-$C_6$)alkylamino, ($C_1$-$C_6$) dialkylamino, ($C_1$-$C_{12}$)alkylthio, carbo ($C_1$-$C_{20}$)alkoxy, carbo($C_1$-$C_{20}$)haloalkoxy, ($C_1$-$C_{12}$)acyl, ($C_1$-$C_6$)alkylcarbonyl($C_1$-$C_6$)alkyl, and the like. Particularly suitable substituted cyclic olefins include maleic anhydride and cyclic olefins containing one or more of hydroxy, aryloxy, ($C_1$-$C_{12}$)alkyl, ($C_1$-$C_{12}$)haloalkyl, ($C_1$-$C_{12}$)hydroxyalkyl, ($C_1$-$C_{12}$)halohydroxyalkyl, carbo ($C_1$-$C_{20}$)alkoxy, and carbo($C_1$-$C_{20}$)haloalkoxy. It will be appreciated by those skilled in the art that the alkyl and alkoxy substituents may be optionally substituted, such as with halogen, hydroxyl, cyano, ($C_1$-$C_6$)alkoxyl, mercapto, ($C_1$-$C_6$)alkylthio, amino or acid labile leaving group. Suitable carbo($C_1$-$C_{20}$)alkoxy substituents include, but are not limited to, those of the formula C(O)O-LG, wherein LG is a leaving group including, but are not limited to, alkyl groups having 4 or more carbon atoms with at least one quaternary carbon atom bonded directly to a carboxylate oxygen such as tert-butyl esters, 2,3-dimethylbutyl esters, 2-methylpentyl esters, 2,3, 4-trimethylpentyl esters, alicyclic esters, acetals or ketals from vinyl ethers or enols such as —O—(CH(CH$_3$)OC$_2$H$_5$) or —O—(CH$_2$OC$_2$H$_5$), tetrahydropyran. Suitable alicyclic esters as leaving groups include adamantyl, methyladamantyl, ethyladamantyl, methylnorbornyl, ethylnorbornyl, ethyltrimethylnorbornyl, ethyl fenchol and the like.

Any of a wide variety of difunctional branch-point monomers are suitable for use in preparing the functional polymers of the present invention provided that such branch-point monomers contain a backbone comprising one or more base cleavable functionalities or moieties, where such functionalities are disposed between the polymerizable groups of the branch-point monomer. By "base cleavable functionality" is meant any functionality or group that can be cleaved by a base such as hydroxide ion, alkoxide ion, ammonia or amines.

A wide variety of difunctional branch-point monomers containing base cleavable moieties may be used. Such branch-point monomers have the structure

A'-Z-B          I where A' and B each include one or more polymerizable groups, and Z includes one or more base cleavable groups. Suitable polymerizable groups for A' and B include, but are not limited to, isocyanate ("—NCO"), $R_{18}R_{19}C=CR$—, $R_{18}$—C≡C—, $R_{18}R_{19}C=CR_{20}C(O)$—O—, $R_{18}R_{19}C=CR_{20}$—O—, and —C(O)—O—$R_{21}$; wherein $R_{18}$, $R_{19}$ and $R_{20}$ are independently selected from H, ($C_1$-$C_4$)alkyl and halo; $R_{21}$ is selected from H, ($C_1$-$C_4$)alkyl, and $NR_{22}R_{23}$; and $R_{22}$ and $R_{23}$ are independently selected from H and ($C_1$-$C_4$)alkyl. In addition to one or more base cleavable groups, the group Z may optionally include one or more spacer groups. Z may suitably have the general formula $S_{x4}(BCG)_{y4}$; wherein S is a spacer group; (BCG) is a base cleavable group; $x_4$=0-20 and $y_4$=1-30. It is preferred that $y_4$=2-20. Suitable spacer groups include, but are not limited to, alkyleneoxy, aryleneoxy, ($C_1$-$C_{20}$)alkylene, substituted ($C_1$-$C_{20}$)alkylene, ($C_6$-$C_{20}$)aralkylene, substituted ($C_6$-$C_{20}$) aralkylene, and the like. Suitable alkyleneoxy groups have the general formula (—CHR$_{24}$-CH$_2$O—)$_{n3}$, (—OCHR$_{24}$-CH$_2$—)$_{m3}$, or (—O—CH$_2$—CH$_2$—CH$_2$—)$_{p3}$, where $R_{24}$ is H or CH$_3$, and $n_3$, $m_3$ and $p_3$ are each 1-1000. Exemplary alkylenoxy groups include ethyleneoxy, propyleneoxy and ethyleneoxy/propyleneoxy mixtures. Aryleneoxy or arylene ether spacers include phenyleneoxy (phenylene ether) spacers having the general formula (—C$_6$H$_4$—O—)$_{z3}$ where $Z_3$=1-1000, biphenylene ethers, phenanthryl ethers, naphthyl ethers, and mixtures thereof. When two or more spacer groups are used, they may be the same or different.

Such spacer groups may be selected to provide additional properties. For example, alkyleneoxy spacers, such as ethyleneoxy and/or propyleneoxy moieties, may help to emulsify the polymeric binders for use in water borne photoresists. Spacers having extended chain length may also provide improved flexibility and be particularly useful in conformal photoresist formulations. The choice of such spacer groups depend upon the particular use of the polymer and the other components in the formulation, and is within the ability of one skilled in the art.

Any base cleavable group is suitable for use in Z, but is preferably selected from anhydrides (—C(O)—O—(O)C—), esters (—C(O)—O—), carbonates, sulfonyl esters (—SO$_2$—O—) and the like, and more preferably esters. It is more preferred that the difunctional branch-point monomers contain 2 or more base cleavable groups and still more preferably 3 or more base cleavable groups. Particularly suitable difunctional branch-point monomers contain 4 base cleavable groups, and more particularly 4 or more ester linkages. It is further preferred that the difunctional branch point monomer contain as polymerizable end groups moieties that also contain one or more base cleavable functionalities, such as (meth)acrylate esters. When the difunctional branch-point monomers contain 2 or more base cleavable groups, such groups may be directly bonded to each other or may be separated by one or more spacer groups. An exemplary structure for such branch-point monomers having multiple base cleavable groups is A'-(S1)$_{x1}$-(BCG)1-(S2)$_{x2}$-(BCG)2-(S3)$_{x3}$-B, wherein S1, S2 and S3 refer to spacer groups 1-3, respectively, (BCG)1 and (BCG)2 refer to base cleavable groups 1 and 2, respectively, x1+x2+x3=0-20, and A', B, S, (BCG) and B are as defined above. Other suitable structures having more or fewer spacers and/or base cleavable groups or different configurations of such groups are well within the ability of those skilled in the art.

Suitable difunctional branch-point monomers useful in preparing the polymers of the present invention include, but are not limited to, acrylic anhydride, methacrylic anhydride, and ester linkage containing monomers having (meth)acrylate end groups. Exemplary difunctional branch-point monomers including one or more urethane linkages and having (meth)acrylate end groups are: pdmbi-pcp0200-pdmbi, pdmbi-pcp0201-pdmbi, pdmbi-pcp0230-pdmbi, eh6c14-hdi-ppg1000-hdi-eh6c14, eh6c14-hdi-pcp0230-hdi-eh6c14, eh6c14-hdi-ppg425-hdi-dmpa-hdi-ppg425-hdi-eh6c14, 2hema-hdi-pcp0230-hdi-ppg425-hdi-pcp0230-hdi-2hema, 2hema-hdi-pcp0230-hdi-peg400-hdi-pcp0230-hdi-2hema, 2hema-hdi-pcp0200-hdi-pcp0230-hdi-pcp0200-hdi-2hema,
e6hem-hdi-pcp0200-hdi-pcp0230-hdi-pcp0200-hdi-e6hem,
e6hem-hdi-pcp0200-hdi-ppg1000-hdi-pcp0200-hdi-e6hem,
e6hem-hdi-pcp0425-hdi-pcp0230-hdi-ppg425-hdi-e6hem,
e6hem-hdi-ppg1000-hdi-pcp0230-hdi-ppg1000-hdi-e6hem,
e6hem-hdi-pcp0230-hdi-ppg425-hdi-pcp0230-hdi-e6hem,
and e6hem-hdi-ppg1000-hdi-pcp0201-hdi-ppg1000-hdi-e6hem. In the above described difunctional branch-point monomers, each "dash" represents a urethane group (formed when an isocyanate group reacts with a hydroxyl group) between the adjacent moieties. Such urethane linkages are not required in the present branch-point monomers. The abbreviations for the moieties are: hdi=1,6-hexamethylene diisocyanate; pcp0200=TONE™ Polyol 0200 Diol (containing carboxylic ester groups); pcp0201=TONE™ Polyol 0201 Diol (contains carboxylic ester groups); pcp0230=TONE™ Polyol 0230 Diol (contains carboxylic ester groups); ppg425=polypropylene glycol having a molecular weight of approximately 425; ppg1000=polypropylene glycol having a molecular weight of approximately 1000; dmpa=dimethylolpropionic acid; pdmbi=3-isopropenyl-alpha, alpha-dimethylbenzyl isocyanate; 2hema=2-hydroxyethyl methacrylate (contains ester group and a polymerizable end group); e6hem=ethoxylated hydroxyethyl methacrylate (contains ester group and a polymerizable end group); and eh6c14=ethoxylated caprolactone-derived methacrylate (contains ester groups and a polymerizable end group). Such branch-point monomers are generally commercially available or may be readily prepared by known methods. TONE™ is a trademark for polycaprolactone diols, available from the Dow Chemical Company (Midland, Mich.). Other suitable polycaprolactone diols are available from Solvay under the CAPA brand name. Typically, the molecular weight of the branch-point monomers is ≧450, and preferably from 450 to 6000.

More than one difunctional branch-point monomer may be used to prepare the functional polymers. Thus, mixtures of difunctional branch-point monomers may advantageously be used in the present invention. The total amount of such difunctional branch-point monomers in the functional polymers may be from 0.1 to 100 wt % based upon the total weight of the monomers used to prepare the polymer, typically from 0.1 to 25 wt %, and more typically from 0.1 to 10 wt %.

Polymers of the present invention contain sufficient acid functionality to render the polymers soluble and removable upon development. The term "acid functionality" refers to any functionality capable of forming a salt upon contact with alkaline developer, such as dilute alkaline aqueous sodium or potassium hydroxide, e.g. 1 to 3 wt % solutions. Suitable acid functionality includes, but is not limited to, carboxylic acids, sulfonic acids, phosphonic acids and phenols. The polymers have an acid number of up to 250, preferably up to 200. Typical ranges of acid numbers are from 15 to 250 and preferably from 50 to 250. Such acid numbers are based on the amount of KOH (potassium hydroxide) in mg to neutralize 1 g (dry weight) of polymer.

Preferably, functional polymers of the present invention have multiple ester links in the backbone or in pendent side chains, or in the backbone and in the pendent chains. Such ester links permit quick and clean removal of the functional polymers from a substrate using a stripping agent. Quick and clean removal is highly desirable in a dry film photoresist. Preferably, functional polymers have from 2 or more ester links in the backbone or in the pendent side chains or in the backbone and chains. Preferably the functional polymers have from 5 or more ester links, more preferably from 10 to 50 ester links, most preferably from 20 to 40 polyester links in the backbone and/or pendent side chains. Such polyester links may be derived from the hydroxy poly opened-ring lactone or hydroxy polyalkylene oxide (meth)acrylates described above.

In one embodiment of the present invention, isocyanate compounds used to prepare the functional polymers of the present invention include urethane/ethylenically or acetylenically unsaturated isocyanates. Such compounds have a —NHC(O)— moiety, at least one free isocyanate group (—N=C=O), and an ethylenically or acetylenically unsaturated moiety such as a (meth) acrylate that is at a terminus of the isocyanate compound. Biuret ethylenically or acetylenically unsaturated isocyanates have a —NH—C(O)—N—C(O)—NH— moiety, at least one free isocyanate group and an ethylenically or acetylenically unsaturated moiety at a terminus of the compound. Examples of such compounds include, but are not limited to, the following general formulas:

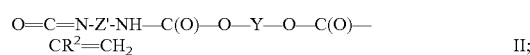

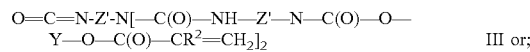

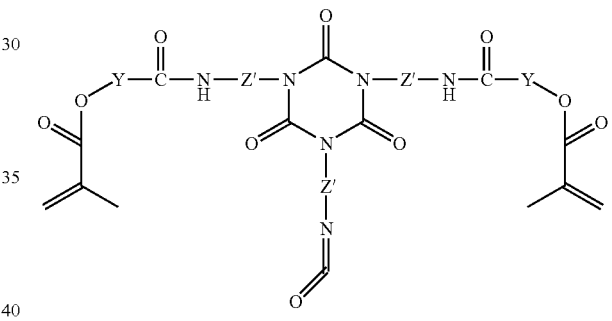

where Z' includes, but is not limited to, alkyl, alkylene, cycloalkyl, aryl, heterocyclic alkyl, heteroaryl, a polymer such as a copolymer including a branched polymer or branched copolymer; Y includes, but is not limited to, alky, alkylene, cycloalkyl, aryl, heterocyclic alkyl, heteroaryl, $-((CH_2)_u-O-)_v-(CH_2)_w-$, or $((CH_2)_u-C(O)-O-)_v-(CH_2)_w-$, where u, and w are integers of from 1 to 10, and v is an integer of from 0 to greater than 1,000, preferably from 1 to 200, most preferably from 5 to 10. $R^2$ is hydrogen or or $(C_1-C_4)$ alkyl. Preferably $R^2$ is hydrogen or methyl. Hetero-atoms include, but are not limited to, oxygen, sulfur, and nitrogen. The alkyl, alkylene, cycloalkyl, aryl, heterocyclic alkyl, heteroaryl and polymers may be unsubstituted or substituted. Examples of suitable substitutent groups include, but are not limited to, carboxyl, hydroxyl, $(C_1-C_4)$ alkyl), aminyl such as a primary or secondary aminyl, or hydroxyaminyl, or —CN.

Examples of suitable alkyl groups include, but are not limited to, linear or branched $(C_1-C_{20})$ alkyl. Examples of alkenyl, cycloakyl or aryl groups include, but are not limited to, linear or branched $(C_2-C_{20})$ alkenyl, $(C_5-C_6)$ cycloalky such as an isophorone, and $(C_5-C_6)$ aryl such as phenyl.

The isocyanate compounds with at least one free isocyanate group may be prepared by any suitable method known in the art. Monoisocyanates with functional groups such as (meth)acrylates, diisocyanates or triisocyanates that may be employed are either known or may be prepared by analogy to known compounds. Examples of suitable diisocyanates and triisocyanates include, but are not limited to, ethylene diisocyanate, propylene diisocyanate, butylene-1,3-diisocyanate, 1,6-hexamethylene diisocyanate, 2,2,4-trimethyl-hexamethylene diisocyanate, 2,4-dimethyl-6-ethyloctamethylene diisocyanate, cyclohexylene diisocyanate, cyclopentylene diisocyanate, 1,4-diisocyanatomethyl-cyclohexane, 1,3-diisocyanatoethyl-cyclohexane, toluylene diisocyanate, 3,3,5-trimethyl-1-isocyanato-5-isocyanatomethyl-cyclohexane, 2-butene-1,4-diisocyanate, isophorone diisocyanate, 1,6-hexamethylene diisocyanate biuret, 1,6-hexamethylene diisocyanate trimer, or isophorone diisocyanate trimer. Many of the foregoing listed diisocyantes and triisocyantes as well as the biurets and trimers may be purchased from Lyondell (located at 122 Melanney St., Houston, Tex.) or Bayer (located at 100 Bayer Rd., Pittsburg, Pa. 15025).

Isocyanates such as the diisocyanates and triisocyanates described above may then be reacted with a sufficient amount of one or more hydroxyl containing compounds such that one free isocyanate group is left to react with the polymer backbone prepared as described above. As mentioned above, the reaction mole ratio of hydroxyl group to isocyanate group is about 1:1. Any suitable compound with at least one free hydroxyl group to react with an isocyanate group may be employed. An isocyanate compound of the present invention also may be reacted with another isocyanate compound having at least one free hydroxyl group. Hydroxyalkyl, hydroxyalkenyl, hydroxyaryl compounds and the like are examples of such compounds that may be employed. Hydroxyalkyl (meth)acrylates are one example of suitable compounds. Hydroxyethyl (meth)acrylate or hydroxypropyl (meth)acrylate (n or iso compounds) are examples of hydroxyl group-containing esters that are suitable. Other suitable hydroxyalkyl (meth)acrylates include, but are not limited to, 2-hydroxy-butyl (meth)acrylate, 4-hydroxy-butyl (meth)acrylate, 2-hydroxy-cyclohexyl (meth)acrylate, 2-hydroxyethylmethacrylate, and the like. Suitable polyethylene glycol mono (meth)acrylates also may be employed such as, but not limited to, diethylene glycol mono (meth)acrylate, triethylene glycol mono (meth)acrylate and the like. Hydroxyalicyclic (meth)acrylates, and hydroxyaromatic (meth)acrylates such as bis phenol A dimethacrylate also may be employed. U.S. Pat. No. 4,019,972 discloses a method of preparing urethanes that may be employed to practice the present invention.

Functional groups that are to be joined to the polymer backbone and have free reactive groups, such as isocyanate groups, may be reacted with compounds having α,β-ethylenically or acetylenically unsaturated groups to extend the functional pendent groups. Such compounds with unsaturated groups include but are not limited to a compound having a formula:

$$CH_2=CHR^3-C(O)-O-(A_1)-(B_1)-(C_1)-H \qquad V$$

where $R^3$ is hydrogen or methyl, $(A_1)$, $(B_1)$ and $(C_1)$ are in any order, $(A_1)$ is a chain formed of from 1 to 40 alkoxylate monomers, aromatic-substituted alkoxylate monomers having from 1 to 20 carbon atoms, or mixtures thereof, $(B_1)$ is either absent or is a chain formed of from 1 to 40 alkoxylate monomers, or aromatic-substituted alkoxylate monomers having from 1 to 20 carbon atoms, or mixtures thereof, and the monomer composition of $(B_1)$ being different than the monomer composition of $(A_1)$, and $(C_1)$ is a chain formed of from 1 to 40 open-ring lactone monomers having from 2 to 21 carbon atoms.

In addition to unsaturated groups, functional polymers generate a free-radical upon exposure to actinic radiation. Free-radical generating monomers or oligomers may be derived from Michael addition reactions of at least one diketone or at least one acetoacetate derivative functional donor compound and at least two multifunctional acrylate receptor compounds. The resulting free-radical generating oligomer may contain both capping and pendent acrylate groups which are capable of cross-linking upon exposure to actinic radiation. Michael addition reactions are catalyzed by a strong base such as diazabicyclo-undecene (DBU). Other cyclic amidines, for example diazabicyclo-nonene (DBN) and guanidines, also are suitable for catalyzing Michael addition reactions. U.S. Pat. No. 5,945,489 and U.S. Pat. No. 6,025,410 disclose Michael addition reactions. Preferably, the oligomers which generate a free-radical absorb light at 300 nm or greater. Such oligomers may be part of the polymer backbone or joined to a pendent group.

A hydrophilic compound which generates a free-radical polymerization initiator of the present invention may have a general formula:

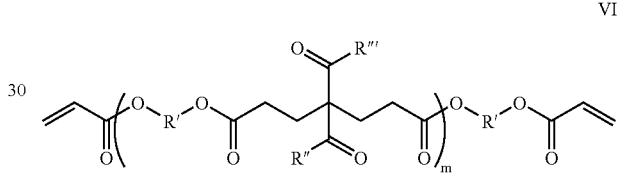

VI where m is an integer of from at least 1, generally from 1 to 100, preferably from 5 to 50, R" and R'" may be the same or different and may be groups that provide the oligomer with water-solubility or water-dispersable, R" and R'" may include, but are not limited to unsubstituted or substituted $(C_6$-$C_{14})$aryl such as unsubstituted or substituted phenyl, unsubstituted or substituted naphthyl, unsubstituted or substituted anthracenyl, unsubstituted or substituted phenanthryl, linear or branched $(C_1$-$C_{15})$alkyl, linear or branched $(C_2$-$C_{15})$hydroxyalky, substituted or unsubstituted $(C_5$-$C_{14})$ heterocyclic aryl where the heteroatom is S, N, or O, or linear or branched $(C_1$-$C_5)$ aminylalkyl, —$NR_9R_{10}$ where $R_9$ and $R_{10}$ are the same or different and may be hydrogen, $(C_1$-$C_3)$alkyl or $(C_1$-$C_4)$hydroxyalkyl. Substituents include, but are not limited to, $(C_1$-$C_5)$alkoxy, hydroxyl, $(C_1$-$C_5)$ hydroxyalkyl, $(C_1$-$C_5)$alkyl, $(C_1$-$C_5)$carboxyalkyl, $(C_2$-$C_5)$ ester, $(C_1$-$C_5)$aminylalkyl, phenyl, hydroxyphenyl, —$NO_2$, sulfonate, phosphate, —SH, $(C_1$-$C_5)$thioalkyl, acetyl, benzoyl, aldehyde, $(C_1$-$C_5)$ketyl, and the like. Preferably, R" or R'" is unsubstituted or substituted phenyl, unsubstituted or substituted naphthyl, unsubstituted or substituted anthracenyl, (C1-C8)alkyl, $(C_2$-$C_{10})$hydroxyalkyl, unsubstituted or substituted $(C_5$-$C_{10})$ heterocyclic aryl, or $(C_1$-$C_5)$aminylalkyl. R" and R'" also may be —O—$R_{11}$ where $R_{11}$ is the same as R" and R'" described above.

R", R'" and $R_{11}$ groups also may absorb light at 300 nm to 365 nm or greater. The most preferred R", R"∝ and $R_{11}$ are water-soluble or water-dispersable and absorb light at 300 nm to 365 nm or greater.

R' also may be a water-soluble or a water-dispersable group. R' may be a group which provides sufficient acid groups such that the polymer may be developed with an aqueous or aqueous base solution. R' may have an acid number of at least 50. Preferably, R' is water-soluble or water-dispersable and absorb light at 300 nm or greater. R' may be derived from acid functional monomers, non-acid functional monomers, alkylene oxides, polyesters, urethanes, or mixtures thereof. Urethanes are compounds that have at least one —CO(NH)— moiety, and biurets are urethanes that have at least one —NH—CONH—CONH— moiety in the structure. Examples of suitable oligomers are disclosed in U.S. Pat. No. 6,045,973, U.S. Pat. No. 6,166,245, U.S. Pat. No. 6,207,347 B1, U.S. Pat. No. 6,268,111 B1, U.S. Pat. No. 6,319,653, U.S. Pat. No. 6,322,951 B1, and U.S. Pat. No. 6,329,123 B1.

While not being bound by theory, it is believed that the pendent ketone substituents, as shown in formula VI, are the source of the free-radical polymerization initiator. Such pendent ketone substituents are integral to the compound and are internal or "built-in" photoinitiators. Integral means that the ketone substitutent is a basic structural component of the compound.

In another embodiment of the invention a source of the free-radical may be a photoinitiator compound. Examples of such photoinitiators include, but are not limited to, imidazole dimers, benzophenones, acetophenones, anthraquinones, naphthaquinones, thioxanthones, ketals, benzoin ethers, or triazine-based compounds. Imidazole dimers such as heaxaarylbiimidazoles (HABI) are very useful in photosensitive formulations such as in photoresists.

A hexaarylbiimidazole with a reactive group which may undergo an addition or condensation reaction with a reactive group of a carrier component as described above has a general formula:

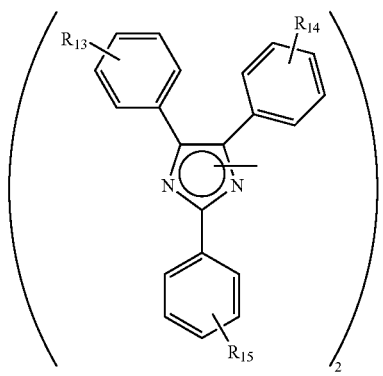

VII $R_{13}$, $R_{14}$ and $R_{15}$ are the same or different and may be a hydrogen, unsubstituted or substituted alkyl, alkoxy, unsubstituted or substituted aryl, aryloxy, hydroxyl, aminyl, carboxyl, ester, thio, isocyanate, —N(CH$_2$—CH$_3$)$_2$, hydroxyalkyloxy or alkylthio. At least one of $R_{13}$, $R_{14}$ and $R_{15}$ is a reactive group which may react with a reactive group of the carrier compound. Such reactive groups may have a labile hydrogen, such as in hydroxyl or aminyl groups. Examples of reactive groups include, but are not limited to, —N(CH$_2$—OCH$_3$)$_2$, carboxyl, ester, thio or isocyanate. Examples of spacer groups with reactive groups include, but are not limited to, ($C_1$ to $C_{12}$)hydroxyalkyl, ($C_1$ to $C_{12}$) carboxyalkyl, ($C_1$ to $C_{12}$)aminylalkyl, ($C_1$-$C_{12}$)alkylester, or hydroxyalkyloxy such as —(O—CH$_2$—CH$_2$)OH, —(O—CH$_2$—CH$_2$—CH$_2$)OH and —(O—CH$_2$—CH$_2$—CH$_2$—CH$_2$)OH, ($C_1$ to $C_{12}$)aliphatic isocyanate, ($C_5$-$C_8$)cycloaliphatic isocyanate or ($C_5$ to $C_6$) aromatic isocyanate.

Any aliphatic, aromatic or cycloaliphatic group with a reactive group attached to it may perform as a spacer group. Preferably, the reactive group is joined to the photoinitiator by a spacer group. A spacer is preferred because bonding the photoinitiator to the carrier component is easier and less disruptive of the photoinitiator capability to form a polymerization initiator. Preferred reactive groups are ($C_1$ to $C_6$)hydroxy alkyl or ($C_1$ to $C_6$)aminyl alkyl. In addition to $R_{15}$ equaling $R_{13}$ and $R_{14}$, $R_{15}$ also may be a halogen group such as chloro, bromo, or fluoro.

Examples of alkyl groups having 1 to 4 carbon atoms are methyl, ethyl, n-propyl, iso-propyl, n-butyl, iso-butyl and test-butyl. Examples of suitable aryl groups having from 6 to 10 carbon atoms are phenyl, naphthyl, ortho-tolyl, meta-tolyl and para-tolyl. Both the alkyl and the aryl groups may be functionalized with a reactive group such as hydroxyl, aminyl or other reactive groups discussed above.

Hydrophobic photoactive compounds may be prepared by any suitable method known in the art. For example, hexaarylbiimidazole compounds may be prepared by oxidative coupling of triphenylimidazoles. Preparation of substituted triphenylimidazoles is described in U.S. Pat. No. 3,748,557, U.S. Pat. No. 4,311,783, and U.S. Pat. No. 4,622,286. In some cases, reaction mixtures in which more than one hexaarylbiimidazole is produced can be used without complete separation and purification as described in U.S. Pat. No. 4,622,286.

An example of forming substituted triphenylimidazoles used in the oxidation procedures to prepare the hexaarylbiimidazoles can be prepared by refluxing, in glacial acetic acid containing ammonium acetate, benzil with an appropriately substituted benzaldehyde or a benzil and benzaldehyde which are both suitably substituted, then drowning the reaction mass in water or in an ammoniun hydroxide solution, filtering and purifying the product by recrystallization; or by refluxing a benzoin and a benzaldehyde in methanol in the presence of copper acetate and ammonia; or by heating a benzil and a benzaldehyde at 180° C. to 190° C. in formamide as described in U.S. Pat. No. 3,784,557. Benzils and substituted benzils may be prepared by any suitable method in the literature such as by oxidizing corresponding benzoins as disclosed in U.S. Pat. No. 4,144,156.

Another method for forming a photoinitiator component with a reactive group is to react the photoinitiator, such as hexarrylbiimidazole, with an alkyl ether or ester in a Friedal Crafts reaction. The ether or ester group on the alkyl chain or spacer group attached to the photoinitiator is cleaved to get a hydroxyl group on the spacer group. The photoinitiator may then be reacted with a reactive group on a carrier component by an addition or condensation reaction to form a photoinitiator of the present invention. Such addition and condensation reactions, as well as the conditions under which they proceed, are well known in the art. Other photoinitiators such as thioxanthones, ketals, benzoin ethers, benzophenones, acetophenones, anthraquinones, napthaquinones and triazine-based compounds may be functionalized with reactive groups by analogy using similar procedures.

Examples of such addition reactions that may occur include the reaction of a hydroxyl, carboxyl or aminyl reactive group on the photoinitiator or joined to the photoinitiator by a spacer group with an isocyanate pendent group on the carrier component to obtain a urethane (—NH-COO—), amide (—NHCO—) or urea bond (—NH-CONH—) between the carrier component and the photoinitiator. Alternatively, an isocyanate group attached to the photoinitiator, or an isocyanate group joined to the photoinitiator by a spacer may react with a hydroxyl, carboxyl or aminyl functional group on the carrier component to form the same types of urethane, amide and urea bonds. Examples of suitable isocyanates which may be employed are described above. Ester bonds (—COOR) also may form to join a photoinitiator to a carrier such as a reaction between an acid group and an alcohol group. R represents an organic moiety described above.

In addition to the photoinitiators described above, aromatic chromophores may be employed in the present invention. Aromatic chromophores have groups such as phenyl and naphthyl, which are sensitive to light at wavelengths of from 320 nm to 450 nm. Typically, such aromatic chromophores are light sensitive from 340 nm to 400 nm, more typically from 350 nm to 365 nm. While not being bound by any theory, it is believed that the aromatic groups of the chromophore provide the light sensitivity in the range of 320 nm to 450 nm. Examples of such aromatic chromophores include, but are not limited to, phenylacridine, or substituted phenylacridines. Such aromatic chromophores may be joined to a polymer by the same methods that the photoinitiators described above may be joined to a polymer.

Examples of other suitable compounds include, but are not limited to, plasticizers, surfactants, and complex surfactants. One example of a suitable plasticizer which may be bonded to a chain or backbone of a functional polymer is a urethane plasticizer having formula VIII.

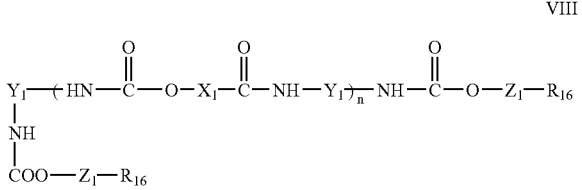

VIII wherein
—$X_1$— is one of the following groups:

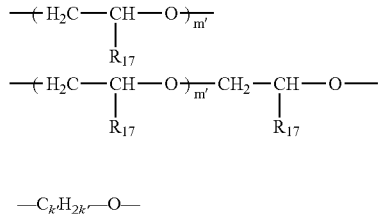

and

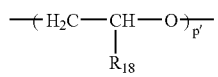

$Y_1$ is a saturated apliphatic or cycloaliphatic group with 2 to 12 carbon atoms,
$Z_1$ is the group

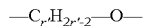

$R_{16}$ is $R_{19}$ or CONH—$R_{19}$,
$R_{17}$ and $R_{18}$ are hydrogen atoms or methyl groups,
$R_{19}$ is a saturated aliphatic group with 1 to 20 carbon atoms, n is zero or a whole number from 1 to 15,
m' is whole number from 2 to 4,
p' is zero or a whole number from 1 to 4,
k' is a whole number from 2 to 12,
r' is a whole number from 4 to 12, and
n'+p' is a whole number from 1 to 10, and wherein $R_{16}=R_{19}$ if p'=0, $R_{16}$=CONH—$R_{19}$ if n'=0.

Because the urethane of formula VIII terminates in aliphatic or cycloaliphatic groups, a functional group such as a halogen may be added to at least one of the terminal groups in order for the urethane to react with a polymer backbone or pendent group.

Examples of water-soluble or water-emulsifiable surfactants that may be joined to a polymer include alkoxylated emulsifiers and alkylglycosides or alkylpolyglycosides. A suitable alkoxylated emulsifier is one having the general formula:

$$R_{20}\text{—O—(A''O)}_n\text{—H} \qquad \text{IX}$$

where A"O are alkylene oxide units selected from ethylene oxide units ($CH_2$—$cH_2$—O) and propylene oxide units (CH($CH_3$)—$CH_2$—O) or ($CH_2$—CH($CH_3$)—O) and mixtures of ethylene and propylene oxide units, either in the mixture of molecules, where $R_{20}$ is a hydrophobic group, typically a hydrocarbon group, n" is between 8 and 200, preferably between 15 and 40. Preferably, $R_{20}$ is a tristyrylphenol.

Dyes may also be joined to functional compounds of the present invention. Suitable dies include, but are not limited to, triphenylmethane dyes, azo dyes, polyazo dyes, antraquinone, eosin, eosinate, thiazine, fluoroscein, phthalein, xanthene, oxazine, aniline based, anionic and cationic dyes. Such dyes may be joined to the functional polymer by any suitable method in the art. Such dyes have one or more free reactive groups, for example, sulfinate, amino, or hydroxyl groups that may react with a group on the polymer. An exemplary method of joining a dye to a polymer is to place a spacer group on one of the ring structures of the dye molecule employing a Friedal Crafts reaction as described above for the photoinitiators. Once the dye molecule has a spacer groups, the reactive group on the spacer is then reacted with a reactive group of a functional polymer as described above.

The functional polymers have an average molecular weight range of at least 1000 daltons. More typically, the molecular weight range of the functionalized polymers is from 10,000 daltons to 500,000 daltons. Molecular weights may be measured by such methods as GPC (gel permeation chromatography) or SEC (size exclusion chromatography). The functionalized polymers of the present invention may be functionalized with one or more pendent functional moieties in ranges of from 1.0 to as high as 100 mole percent of reactive sites on the polymer backbone, preferably from 2.0 to 20 mole percent, most preferably from 5.0 to 15 mole percent. Complete functionalization of the polymer backbone with pendent groups is not always desirable because such groups as hydroxyl and carboxyl groups on the backbone provide for solubility in alkaline solutions. Such solubility is highly desirable when the functionalized polymer is employed in photoresist.

The functionalized polymers of the present invention are film forming polymers that form films that are flexible, and may be employed in any industry where dry film coatings are desired. Such industries include, but are not limited to lithography, and electrophotographic imaging members. The functionalized polymers also have good flexibility, and are readily soluble in aqueous alkaline solutions such as sodium hydroxide, potassium hydroxide, sodium carbonate, and the like. Because the functionalized polymers have good flexibility and solubility, the functionalized polymers are especially useful in dry film photoresist compositions, particularly in primary imaging photoresists. The high solubility of the functionalized polymers in aqueous alkaline solutions enables photoresists made with the functionalized polymers to be easily stripped. The improved stripping ability eliminates or significantly reduces the problem of short circuiting on circuit boards. Additionally, undesirable and costly strippers such as organic-based, amine or organic solvent-containing strippers may be avoided. Thus, excessive waste treatment procedures may be eliminated from the printed wiring board procedures as well as environmental and worker safety concerns associated with such organic-based strippers. Good flexibility also provides for a photoresist that is not brittle and does not readily chip. Chipping, due to brittleness, can lead to circuit defects in printed wiring boards.

The functionalized polymers also have good adhesion to metal surfaces due to their pendent functional groups. The functionalized polymers are also self-cross-linking, thus the functionalized polymers may be employed as the sole cross-linking agent in a photoresist composition. Advantageously, cross-linking monomers or oligomers employed in conventional photoresists may be eliminated. Thus, premature polymeriztion between the various components of a photoresist composition are avoided. Accordingly, both the stability and the shelf life of such photoresists are improved.

The functionalized polymers of the present invention may be employed in both primary imaging photoresists or in secondary imaging photoresists such as in solder masks. Although the functionalized polymers may act as both the binder polymer for the photoresist as well as the sole cross-linking agent in the photoresist composition, optional cross-linking monomers or oligomers may be added to the photoresist composition. Functionalized polymers of the present invention compose from about 65% by weight to about 95% by weight of the photoresist composition. Typically the functionalized polymers comprise from about 75% by weight to about 90% by weight of the photoresist composition. The balance of the photoresist composition may include additional binder polymers, cross-linking monomers or oligomers, and adjuvants described below.

Optional cross-linking agents may be employed, but are preferably excluded. Such cross-linking agents include a monomer, or a short chain oligomer having ethylenic unsaturation, particularly, α,β-ethylenic unsaturation functionality of 2 or greater. A mixture of conventional monofunctional and multi-functional monomers may be used. Such optional cross-linking agents are included in amounts of from 5% to 15% by weight of the photoresist.

Optionally of the functionalized polymers of the present invention may contain an additional photoinitiator chemical system. Preferably such photoinitiators are excluded. The photoinitiator chemical system may compose from 0.1% to 5% by weight of the photoresist composition. Conventional photoinitiators or photoinitiator systems may be employed.

Photoresist compositions of the present invention may also include an optional color former. Color formers are employed in amounts of from 0.1% to 1.0% by weight of the composition. Examples of suitable color formers include, but are not limited to, diphenylamine, dibenzylaniline, triphenylamine, diethylaniline, diphenyl-p-phenylenediamine, p-toluidine, 4,4'-biphenyldiamine, o-chloroaniline, leuco crystal violet, leuco malachite green, and the like.

Additionally, the photoimageable compositions may contain a wide variety of additional adjuvants including stabilizers, flexibilizing agents, adhesion promoters, plasticizers, fillers or mixtures thereof. Such adjuvants are additives that contribute to the effectiveness of the primary ingredients. A wide variety of additional polymeric or resin binders may be added to the photoresists. Such additional polymeric binders may include, as polymerized components, one or more acid functional monomers such as (meth)acrylic acid, for example as disclosed in U.S. Pat. No. 5,952,153. When employed, such polymers may be used in amounts of from 10% to 20% by weight of the photoresist.

Processing of the photoresist compositions is by any suitable means employed in the art. For example, the dry film is composed of a liquid photoimageable composition dried onto a flexible sheet, e.g., polyethylene terephthalate. Optionally, a protective sheet, e.g., polyethylene, is provided on the surface of the dried photoimageable layer opposite the support sheet before the film is rolled into reels. The protective sheet is removed prior to application, e.g., lamination, to the metal-clad board. Once applied, the photoimageable composition layer is then exposed to actinic radiation through appropriate artwork. Exposure to actinic radiation polymerizes the cross-linking components in the light-exposed areas resulting in a cross-linked structure that is resistant to developer. Next, the composition is developed in dilute alkaline aqueous solution, such as a 1% sodium carbonate solution. The alkali solution causes salt formation with carboxylic acid groups of the functionalized polymer rendering the unexposed portions of the photoresist soluble and removable. After development, an etchant may be used to remove metal from areas where the photoresist was removed thereby forming a printed circuit. The remaining photoresist may be then removed using an appropriate stripper, such as 1% to 3% sodium or potassium hydroxide aqueous solution. Organic based developers, such as tetraalkylammonium hydroxide based developers, may be used but are less preferred for the reasons discussed above.

The following examples are intended to further illustrate the present invention but are not intended to limit the scope of the invention.

EXAMPLE 1

To 2.1 parts of hydroxybutyl substituted benzil (0.01 mole) dissolved in 50 parts of glacial acetic acid containing 6 parts of ammonium acetate (0.078 mole) is added 1.4 parts of o-chlorobenzaldehyde (0.01 mole), and the solution is refluxed for 2 hours. The solution is then drowned in 200 parts of cold water whereupon 3.1 parts of reaction product precipitate. The product is isolated by filtration and purified by recrystalling twice from ethanol. The product, a chlorinated hydroxybutyl imidazole, is a white crystalline solid.

To 1.1 parts of the above prepared imidazole dissolved in 100 parts of ethanol containing 12 parts of potassium hydroxide is added 450 parts of a 1% by weight water solution of potassium ferricyanide at a rate of 5 parts per minute for 1.5 hours with continuous stirring. The oxidation reaction product in an amount of 1.0 parts precipitates from the reaction mixture, is isolated by filtration, and is washed with water until free from ferricyanide. The product is dried at 56° C. for eight hours at 0.1 mm. mercury pressure after predrying overnight in a vacuum oven at 50° C. It is solvated with two moles of enthanol for every three moles of biimidazole. The product is a biimidazole having the general formula shown below.

A portion of the ethanol-solvated product was dried azeotropically with cyclohexane to produce non-solvated material. Recrystallization from ether also yields the non-solvated product.

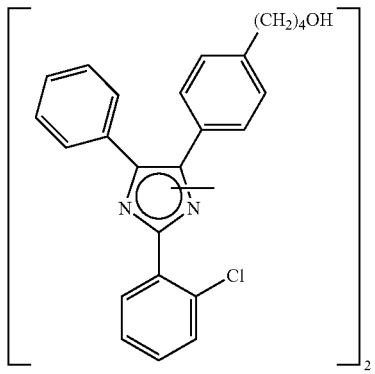

The above photoactive component is then reacted with the pendent carboxyl groups of an oligomer composed of methylmethacrylate and acrylic acid to bind the photoactive component with the oligomer by an ester linkage. The oligomer is prepared by free radical polymerization of the methylmethacrylate and acrylic acid monomers. The methylmethacrylate and acrylic acid monomers are obtainable from Rohm and Haas Company. The reaction takes place in an aqueous acidic environment. The reactants are refluxed in the acidic environment from 90° C. to 100° C. to obtain a water-soluble photoinitiator yield of from 85% to 90% by weight.

The hydrophilic photoinitiator containing compound may be employed as a cross-linking agent or further polymerized and employed as a polymer binder in a photoresist formulation. Upon exposure to light, a radical from the photoactive component is generated to polymerize the cross-linking agents of the formulation.

EXAMPLE 2

Negative-Acting Dry Film Photoresists

The following ingredients are blended together in the given proportions to provide a negative-acting photoresist composition of the present invention.

| Ingredient | Formulation Percent by Weight |
|---|---|
| Acrylic copolymer binder[1] | 40 |
| Caprolactone 2 hydroxyethyl methacrylate | 5 |
| Trimethylol propane triacrylate (TMPTA) | 15 |
| photoinitiator containing compound[2] | 5 |
| bis(dialkylaminophenyl) ketone | 0.04 |
| tris(dialkylaminophenyl) methane | 0.3 |
| aromaticsulfonamide | 3.5 |
| modifideacridine | 0.2 |

Table Footnotes
[1]88,000-91,000 Mw copolymer of methyl methacrylate, methacrylic acid, n-butyl acrylate, Tg 90° C., 150 acid number.
[2]Photoinitiator of Example 1.

A mixture is prepared at about 70% solids in 2-butanone and coated onto a 0.8 mil polyester carrier film and dried to approximately 1% residual VOC's. A thin film of about 1.5 mils thickness is obtained. The films are then laminated at 121° C., 40 psi, 1 meter per minute, onto chemically cleaned 1 oz. copper/0.059 FR-4/1 oz. clad copper laminate and imaged on a 5 kw printer through a silver halide phototool with an adjusted exposure to obtain a copper step of 9 as measured with a Stouffer® 21 step wedge. The panels are then developed in 1% sodium carbonate monohydrate at 29° C. to remove the photoresist in the unexposed portions followed by several spray rinses using tap water and the deionized water. The imaged board is then etched in 2N cupric chloride/HCl at 45° C. The etched boards are then stripped of the imaged and developed photoresist in a 3% sodium hydroxide solution at 49° C., followed by a spray rinse of tap water.

EXAMPLE 3

A radiation curable solder mask composition is prepared in two parts as follows:

| | Percent By Weight |
|---|---|
| Component A | |
| Esterified styrene-maleic anhydride copolymer[1] | 25.0 |
| Photoinitiator containing compound[2] | 5.0 |
| Multifunctional (meth)acrylate[3] | 7.5 |
| Pigment | 4.0 |
| Flow promoter | 3.5 |
| Anti-abrasion agent | 3.5 |
| Air release agent | 3.5 |
| Filler | 17.5 |
| Inert diluent | 10.5 |
| Component B | |
| Multifunctional (meth)acrylate[3] | 25.0 |
| Multifunctional epoxy[4] | 30.0 |
| Thermal cross-linking agent[5] | 7.5 |
| Pigment/filler | 12.5 |
| Inert diluent | 25.0 |

[1]Pro 1100, Sartomer Co., Exton, Pa.
[2]Photoinitiator of Example 1.
[3]SR 351, Sartomer Co.
[4]ECN1299, CibaGeigy Co. (Resin Division)
[5]Dyhard100S, SKW Inc.

Component A and Component B are mixed, in a ratio of 3:1 at room temperature, and the composition so produced is screen-printed onto printed circuit boards using a 70 Durometer squeegee. The boards are then heat treated at 160° F. for various lengths of time to determine the operating window for pre-baking. The pre-baked boards are then subjected to development using a 10 g/L solution of potassium carbonate at 25°-30° C. for 40 seconds. Boards are baked for 50 minutes and exhibit clean removal of the composition with no residual scum is remaining on the board.

Additional printed circuit boards are coated with the composition in the same manner as above, the composition is dried at 70° C. for twenty minutes, cooled to room temperature, and then identically processed to coat the other side of the board (70° C. drying for 40 minutes). Negatives are brought into contact with the coatings, and each coating is then subjected to 150 millijoules of ultraviolet radiation. The coatings are developed using potassium carbonate solution, 25°-30° C. for 40 seconds. The remaining imagewise distribution of photopolymer is then given a post-exposure of 2-4 joules, and then baked for 1 hour at 150° C.

The so-treated coating is tested for flexibility using the cross-hatch razor technique in which several intersecting lines are cut into the coating. The coating is found to be flexible, with no loss of adhesion.

EXAMPLE 4

Synthesis of Functionalized Copolymer

A homogeneous solution containing 197 grams of methacrylic acid, 512 grams of methyl methacrylate and 79 grams of poly(ethoxylated) monomethacrylate was prepared. 75% by weight of the homogeneous solution were prepared into a second flask. The homogeneous solution of the first flask was diluted to 25% by weight solids and the homogeneous solution of the second flask was diluted to 60% be weight solids by adding sufficient methyl ethyl ketone.

The first flask was mixed and heated to reflux under atmospheric conditions. 2.0 grams of 2,2'-azobis (2-methylbutyronitirle) was added to the reaction mixture, mixed and held at reflux for 30 minutes.

6.0 grams of 2,2'-azobis (2-methylbutyronitirle) was mixed with about 40 grams of methyl ethyl ketone and fed into the first flask along with the contents of the second flask over 4 hours while maintaining reflux. An additional amount of 9.0 grams of methyl ethyl ketone was then added to the first flask and the mixture was refluxed for an additional hour.

5.0 grams of 2,2'-azobis (2-methylbutyronitrile) were dissolved in 50.0 grams of methyl ethyl ketone and mixed. The mixture was then added to the first flask over a period of 90 minutes while maintaining reflux.

9.0 grams of 2,2'-azobis (2-methylbutyronitrile) were mixed with 50.0 grams of methyl ethyl ketone and then fed into the reaction mixture over 150 minutes while maintaining reflux. An additional amount of 25.0 grams of methyl ethyl ketone were added to the reaction mixture. At the end of the reaction, 2,2'-azobis (2-methylbutyronitirle) was thermally killed off to below parts per million concentrations. The acrylic copolymer main chain or backbone was set aside.

5.31 grams of 1,6-hexamethylene diisocyanate biuret (23.% free-NCO) were added to a clean dry, nitrogen sparged flask. 0.06 grams of dibutylin dilaurate, 0.05 grams of Irganox® 1076 (antioxidant) and 160.0 grams of methyl ethyl ketone were also added to the flask. The flask was sparged with dry air and stoppered. The components were mixed and heated at 35° C.

In a separate clean dry air sparged addition funnel, 15.97 grams of poly(ethoxylate-b-caprolactone) monomethacrylate oligomer was weighed out. The oligomer was added to the flask containing the 1,6-hexamethylene diisocyanate biuret over 1 hour with mixing and maintaining a temperature of 35° C. The addition funnel was then rinsed with 118.0 grams of methyl ethyl ketone to remove any remaining oligomer. The rinse was added to the flask containing the biuret with a temperature increased to 60° C. The reaction was maintained for 3 hours at 60° C. the reaction was monitored to determine completion of the synthesis of a urethane acrylate moiety by high pressure liquid chromatography (HPLC).

The functionalized polymer was prepared by weighing out 763.0 grams of the acrylic copolymer (47% solids) and 50.0 grams of methyl ethyl ketone to a clean, dry air sparged flask. The combination was mixed and heated to 45° C. The urethane/acrylate moiety was then added to the acrylic polymer over 1 hour 0.50 grams of Irganox® 1076 and 30.0 grams of methyl ethyl ketone was added to the reaction mixture. The reaction contents were held at 45° C. for 3 hours with constant mixing. The resulting copolymer was composed of 25 mole % of methyacrylic acid, 65 mole % of methyl methacrylate and 10 mole % of poly(ethoxylated) monomethacrylate residues. The copolymer main chain was 6 mole % functionalized with the moiety.

EXAMPLE 5

Synthesis of a Functionalized Copolymer

A homogeneous solution containing 77.5 grams of 2-hydroxyethyl methacrylate, 194 grams of methacrylic acid, and 504 grams of methyl methacrylate was prepared. 75% by weight of the homogeneous solution was transferred to a second flask. The homogeneous solution of the first flask was diluted to 25% by weight solids and the homogeneous solution of the second flask was diluted to 60% by weight solids by adding sufficient methyl ethyl ketone.

The first flask was mixed and heated to reflux under atmospheric conditions. 2.0 grams of 2,2'-azobis (2-methylbutyronitirle) was added to the reaction mixture, mixed and held at reflux for 30 minutes.

6.25 grams of 2,2'-azobis (2-methylbutyronitirle) was mixed with 40.0 grams of methyl ethyl ketone and fed into the first flask along with the contents of the second flask over 4 hours while maintaining reflux. An additional amount of 9.0 grams of methyl ethyl ketone was then added to the first flask and the mixture was refluxed for an additional hour.

5.0 grams of 2,2'-azobis (2-methylbutyronitrile) were dissolved in 50.0 grams of methyl ethyl ketone and mixed. The mixture was then added to the first flask over a period of 90 minutes while maintaining reflux.

9.0 grams of 2,2'-azobis (2-methylbutyronitirle) were mixed with 50.0 grams of methyl ethyl ketone and then fed into the reaction mixture over 150 minutes while maintaining reflux. An additional amount of 23.0 grams of methyl ethyl ketone were added to the reaction mixture. At the end of the reaction, 2,2'-azobis (2-methylbutyronitirle) was thermally killed off to below parts per million concentrations. The acrylic polymer main chain or backbone product was set aside.

150.0 grams of 1,6-hexamethylene diisocyanate biuret (23.0% —NCO) were added to a clean dry, nitrogen sparged flask. 0.06 grams of dibutylin dilaurate, 0.05 grams of Irganox® 1076 (antioxidant) and 160.0 grams of methyl ethyl ketone were also added to the flask. The flask was sparged with dry air and stoppered. The components were mixed and heated at 35° C.

In a separate clean dry air sparged addition funnel, 190.0 grams of poly(ethoxylate-b-caprolactone) monomethacrylate oligomer was weighed out. The oligomer was added to the flask containing the 1,6-hexamethylene diisocyanate biuret over 1 hour with mixing and maintaining a temperature of 35° C. The addition funnel was then rinsed with 120.0 grams of methyl ethyl ketone to remove any remaining oligomer. The rinse was added to the flask containing the biuret with a temperature increased to 60° C. The reaction was maintained for 3 hours at 60° C. The reaction was monitored to determine completion of the synthesis of the urethane acrylate moiety.

The functionalized polymer was prepared by weighing out 750.0 grams of the acrylic copolymer and 55.0 grams of methyl ethyl ketone to a clean, dry air sparged flask. The combination was mixed and heated to 45° C. The urethane/ arcrylate moiety was then added to the acrylic copolymer over 1 hour. 0.50 grams of Irganox® 1076 and 30.0 grams of methyl ethyl ketone was added to the reaction mixture. The reaction contents were held at 45° C. for 3 hours with constant mixing. The polymer main chain was 6 mole percent functionalized with the moiety.

What is claimed is:

1. A dry film photoresist comprising a polymer having an average molecular weight of at least 10,000 daltons, α, β-unsaturation, and a functional group integral to a backbone of the polymer that generates a free radical upon exposure to actinic radiation, the polymer comprising from 65% by weight to 95% by weight of a dry film photoresist, wherein the polymer is formed from ethylenically or acetylenically unsaturated monomers, oligomers or combinations thereof, said monomers selected from the group consisting of (meth)acrylic acid, (meth)acrylamides, alkyl (meth)acrylates, alkenyl (meth)acrylates, aromatic (meth)acrylates, vinyl aromatic monomers, nitrogen-containing compounds and their thio-analogs, substituted ethylene monomers, cyclic olefins and substituted cyclic olefins, wherein the free radical is generated from a photoinitiator compound joined to the polymer to form the functional group, said photoinitiator compound comprising an imidazole dimer, a thioxanthone, a ketal, a benzoin ether, a benzophenone, an acetaphenone, an anthraquinone, a naphthaquinone, an aromatic chromophore or combinations thereof.

2. The dry film photoresist of claim 1, wherein the polymer further comprises one or more pendent functional groups joined to a backbone of the polymer.

3. The dry film photoresist of claim 2, wherein the free radical is generated from photoinitiator compounds joined to the one or more pendent functional groups joined to the backbone of the polymer.

4. The dry film photoresist of claim 3, wherein the functional groups comprise α, β-unsaturation, stripping agents, plasticizers, surfactants, dyes or combinations thereof.

5. The dry film photoresist of claim 1, further comprising an additional photoinitiator, a dye, a cross-linking agent, or mixtures thereof.

6. The dry film photoresist of claim 1, wherein the dry film is laminated on a substrate and has a cover sheet opposite the substrate.

* * * * *